United States Patent [19]

Close et al.

[11] 4,075,257

[45] Feb. 21, 1978

[54] 3,7,11-TRIMETHYLDODECA-1,2-DIENE

[75] Inventors: Ralph E. Close, Jacksonville, Fla.; William Oroshnik, Plainfield, N.J.

[73] Assignee: SCM Corporation, New York, N.Y.

[21] Appl. No.: 772,264

[22] Filed: Feb. 25, 1977

Related U.S. Application Data

[62] Division of Ser. No. 622,972, Oct. 16, 1975, which is a division of Ser. No. 560,550, March 20, 1975.

[51] Int. Cl.² .......................................... C07C 11/12

[52] U.S. Cl. ............................ 260/680 R; 260/654 R; 260/638 Y; 260/678; 560/242; 260/619 F; 260/617 R

[58] Field of Search .................................... 260/680 R

[56] References Cited

U.S. PATENT DOCUMENTS 3,096,384  7/1963  Logan ............................ 260/680 R Primary Examiner—Delbert E. Gantz
Assistant Examiner—Joseph A. Boska
Attorney, Agent, or Firm—Richard H. Thomas

[57] ABSTRACT

The compound 3,7,11-trimethyldodeca-1,2-diene useful for the synthesis of dehydrophytol and Vitamin E.

1 Claim, 1 Drawing Figure

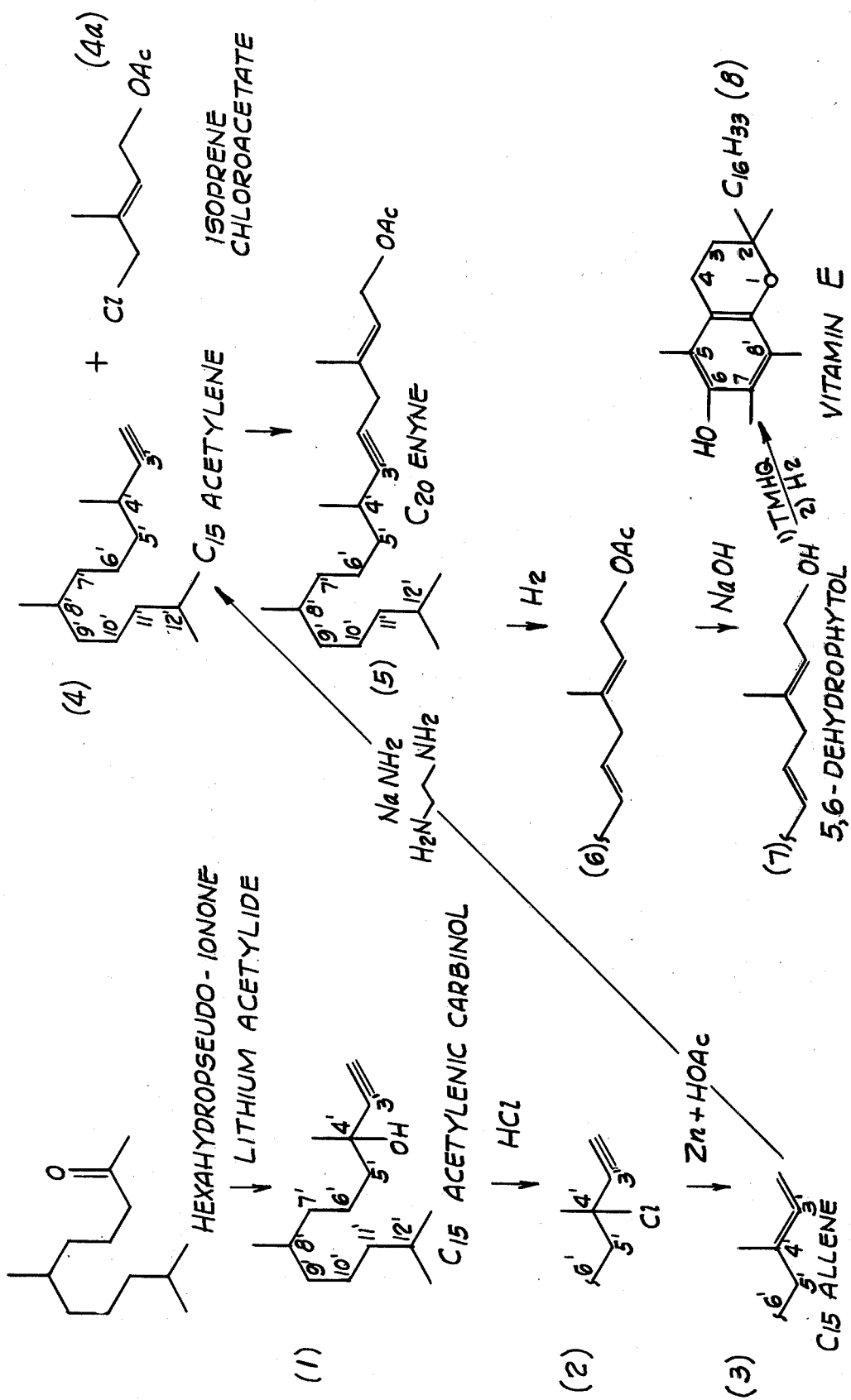

3,7,11-TRIMETHYLDODECA-1,2-DIENE

This application is a division of application Ser. No. 622,972, filed Oct. 16, 1975, which in turn is a division of application Ser. No. 560,550, filed Mar. 20, 1975.

The present invention relates to the synthesis of dehydrophytol (3, 7, 11, 15-tetramethylhexadeca-2,5-dien-1-ol) and the production of Vitamin E therefrom.

BACKGROUND OF THE INVENTION

The synthesis of Vitamin E, that is, alpha-trocopherol (5, 7, 8-trimethyltocol) in the past has been accomplished primarily by reacting trimethylhydroquinone (TMHQ) with isophytol (3, 7, 11, 15-tetramethylhexadec-1-en-3-ol) or phytol (3, 7, 11, 15-tetramethylhexadec-2-en-1-ol) in a condensation reaction. The reaction is well known and has been practiced for many years.

The various routes to phytol and isophytol have been reviewed by Stalla-Bourdillon, *Ind. Chim. Belg.*, 35, 13 (1970); and also in "The Vitamins,"Vol. 5, pages 168–223, Academic Press, New York, 1967. With few exceptions, these routes utilize a $C_{10}$ intermediate (natural or synthetic) and proceed to the $C_{20}$ phytol or isophytol by sequential addition of various carbon units ($C_4$ or less). The steps are numerous, and the syntheses are costly.

In copending application Ser. No. 353,215, filed Apr. 23, 1973, on "Synthesis of Vitamin A Intermediates and Conversion Thereof to Vitamin A," by William Oroshnik, a novel process is disclosed which comprises forming an ethynyl-terminated alkoxy-substituted beta-ionol intermediate from beta-ionone and then coupling such intermediate with a compound like "isoprene chloroacetate" (1-acetoxy-4-chloro-3-methylbut-2-ene) to produce a $C_{20}$ skeleton. The latter by semi-hydrogenation, hydrolysis and treatment with a strong base produced Vitamin A. The invention of copending application Ser. No. 353,215 resides in part in the discovery that successful coupling of the intermediate and isoprene chloroacetate permitted elimination of at least one additional step in the Vitamin A synthesis, The present invention resides in part in the discovery that "isoprene chloroacetate" is also a useful reactant in the synthesis of Vitamin E.

SUMMARY OF THE INVENTION

The present invention resides in an improved and economical process for the production of dehydrophytol and Vitamin E and in particular in a process wherein hexahydropseudoionone is reacted with a metal acetylide in a condensation reaction to form the corresponding $C_{15}$ acetylenic carbinol which in turn through a series of reactions is coupled with isoprene chloroacetate to form a $C_{20}$ acetoxy enyne. The latter by a further series of hydrogenation and saponification reactions forms the compound dehydrophytol. Dehydrophytol in turn couples with trimethylhydroquinone to give dehydro-Vitamin E, which can then be hydrogenated to give Vitamin E.

A feature of the present invention is reductive removal of the hydroxyl group of the $C_{15}$ acetylenic carbinol prior to coupling with isoprene chloroacetate. This is accomplished by first replacing the hydroxyl group with a halogen or alkyl or aryl sulfonate and then subjecting the substituted compound to direct replacement with hydrogen. This latter reaction results in the production of an allene which is rearranged to the desired acetylene.

For purposes of the present application, temperature is in degrees Centigrade and percentages are in terms of percentage by weight, unless otherwise specified.

BRIEF DESCRIPTION OF THE DRAWING

The invention may best be understood with reference to the accompanying drawing in which the FIGURE is a flow diagram illustrating a preferred process for the synthesis of Vitamin E in accordance with the present invention.

The process starts with the reaction of hexahydropseudo-ionone with a metal acetylide to form a hexahydropseudo-iononederivative [formula (1)] having a terminal acetylene group and methyl and hydroxyl groups on the adjacent carbon atom. This compound in a series of novel steps is halogenated and then reacted with zinc and glacial acetic acid to form an corresponding allene [formula (3)], the latter being isomerized in a solution of sodamide in ethylene diamine and ether to form the $C_{15}$ acetylene compound represented by formula (4). Coupling with isoprene chloroacetate to form the basic $C_{20}$ enyne skeleton [formula (5)] is then carried out. for instance, following the teachings of copending application Ser. No. 353,215. Dehydrophytol (7) is obtained by the successive steps of partial hydrogenation of the acetylenic group, and saponification.

In the drawing and following examples, the numbers assigned to the various atoms of the formulae follow the conventional numbering system for tocopherols, both with regard to the product Vitamin E and intermediate compounds preceding Vitamin E. In other words, in the interest of facilitating understanding of the invention, each carbon atom of the intermediate compounds is given that number it will eventually have in the final alphatocopherol molecule. The numbering system for tocopherols can be found in *Methods in Enzymology*, Vol. XVIII, "Vitamins and Coenzymes," Part C, page 242, Donald B. McCormick and L. D. Wright. Academic Press (1971). This does not however apply to the naming of the compounds.

It is also understood that in the following formulae and equations, single bond lines attached to a carbon atom with no atom indicated represent the attachment of a methyl group to the atom.

EXAMPLE

Hexahydropseudo-ionone (note the figure) is an available material produced by complete hydrogenation of the double bonds of pseudo-ionone, e.g., by catalytic hydrogenation. The hexahydropseudo-ionone is reacted with a metal acetylide such as lithium or sodium acetylide, in a known condensation reaction using conventional chemistry to provide 3, 7, 11-trimethyl-3-hydroxy-1-dodecyne (1), a $C_{15}$ acetylenic (ethynyl) carbinol compound having a terminal acetylene group and methyl and hydroxy groups on the adjacent carbon atom. Again, the numbering system applied in the drawing for this formula and succeeding formulae follows the conventional number system for the tocopherols, each carbon atom being given the number it will eventually have in the alpha-tocopherol molecule.

A method for the preparation of compound (1) can be found in the publication F. G. Fisher and K. Lowenberg, *Liebigs Ann. Chem.*, 475, 183 (1929). The subject matter of this publication is incorporated herein by reference. Specific pages of interest are pages 495 and 521.

Halogenation

The carbinol of formula (1) is converted to the corresponding chloride, 3, 7, 11-trimethyl-3-chloro-1-dodecyne (2) by dissolving the carbinol in a concentrated hydrochloric acid solution saturated with dry hydrogen chloride at about $-25°$ to $-10°$. The conversion is carried out at $-10°$ to $0°$, under atmospheric pressure, preferably in the presence of cuprous chloride resulting in a substantially quantitative recovery of the chloride. The product, an acetylenic chloride or propargylic chloride, is a clean water-white oil.

In a particular example, 78.8 grams (0.351 mole) of the $C_{15}$ ethynylcarbinol is added at $-25°$ to a mixture of 550 ml concentrated HCl and 18.5 grams of CuCl into which HCl gas has been bubbled until in excess. After warming to $0°-5°$ and at the end of a reaction period of about 2 hours, the reaction mixture was extracted with pentane and worked-up following conventional procedures to yield 87.3 grams of crude product.

The above reaction can be carried out with any hydrogen halide, e.g., hydrogen bromide, or following other procedures.

Dehalogenation to Allene (3)

The chloride of formula (2) is reductively dehalogenated to the corresponding $C_{15}$ allene, 3, 7, 11-trimethyl-dodeca-1,2-diene, by dissolving and stirring the chloride in a mixture of glacial acetic acid mixed with zinc dust, using the following proportions:

| | |
|---|---|
| $C_{15}$-Propargylic chloride* | 87.3 grams |
| Zinc dust (activated with dilute HCl) | 87.3 grams |
| HOAC (glacial) | 850 ml |

*The crude product from the halogenation step

The reaction is exothermic but is carried out at room temperature by cooling, although this is not critical. Quenching in water after filtering off the unreacted zinc dust, taking up the oil precipitate with a solvent such as hexane, further washing, drying and concentrating, results in a crude product of 80% purity. This is then distilled at 0.5 mm pressure with very little or no polymerization to give a product of 84% purity. The yield of desired product was 85% of theoretical yield.

Rearrangement to $C_{15}$ Acetylene

Although there are many examples of basic reagents for bringing about the isomerization of allenes to acetylenes, a solution of sodium amide (NaNH$_2$) in ethylene diamine (H$_2$N—CH$_2$—CH$_2$—NH$_2$) produces an 87% by weight yield of distilled product of 70% purity. The bulk of the impurity if a conjugated diene.

The reaction is carried out by adding the allene dropwise to a solution of sodium amide (NaNH$_2$) in ethylene diamine-ether (30:70) maintained at room temperature. The reaction mixture is agitated during addition and for about two to three hours thereafter, followed by quenching with aqueous ammonium chloride and distillation.

The presence of the diene does not interfere in the subsequent coupling reaction of the acetylene with "isoprene chloroacetate" (1-acetoxy-4chloro-3-methyl-but-2-ene), as it is merely an inert component in the reaction mixture.

The resultant $C_{15}$ acetylene product is 3, 7, 11-trimethyldodeca-1-yne (4).

In a particular example, the following components were employed:

| | |
|---|---|
| $C_{15}$ allene* | 76.2 grams |
| Na | 13.5 grams (0.59 gram-atoms) |
| NH$_3$ | 700 ml |
| ether (anhydrous) | 700 ml |
| NH$_2$CH$_2$CH$_2$NH$_2$ (dried over molecular sieves) | 280 ml |

*The crude product of dehalogenation step

The ammonia and sodium are combined in the presence of a catalytic amount of Fe (NO$_3$)$_3$.9H$_2$O at the boiling temperature of NH$_3$ to obtain a solution of NaNH$_2$ in liquid NH$_3$. The ether, ethylene diamine and allene are then added in that order. After a reaction period of about 4½ hours, quenching and work up, 54.4 grams of distilled product (63.5% acetylene) was obtained.

Coupling Reaction to the Acetate of the $C_{20}$ Enyne

The compound of formula (4) is coupled with isoprene chloroacetate (1-acetoxy-4-chloro-3-methylbut-2-ene) (4a) to form the basic $C_{20}$ skeleton of dehydrophytol. The chloroacetate is known and prepared by the chlorhydrination of isoprene in glacial acetic acid as described in an article by W. Oroshnik and R. A. Mallory, J. Amer. Chem. Soc. 72, 4608 (1950). It can be represented by the following formula:

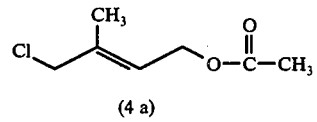

(4 a)

Alternatively, the isoprene chloroacetate may be prepared by the method described in copending application Ser. No. 359,011 filed May 10, 1973, By Carlos G. Cardenas, assigned to assignee of the present application.

The coupling reaction results in the preparation of 3, 7, 11, 15-tetramethyl-1-acetoxyhexadec-2-en-5-yne(5), a $C_{20}$ enyne.

The coupling reaction may be carried out employing several methods. The following methods are preferred.

Method A: This coupling reaction involves pre-forming a cuprous salt of the $C_{15}$ acetylene compound of formula (4) and then reacting the salt with the coupling reactant "isoprene chloroacetate" (4a) in an aprotic solvent such as dimethyl formamide (DNF). The cuprous salt is formed by reacting the $C_{15}$ acetylene compound with a Grignard reagent such as methyl magnesium chloride in the presence of tetrahydrofuran (THF) giving off methane as a gas to form an acetylenic Grignard compound and then adding cuprous chloride, copper replacing the magnesium chloride group. Following this, isoprene chloroacetate dissolved in DMF is added; and the tetrahydrofuran is driven off under vacuum leaving a DMF solution in which all the reactants are dissolved. This solution is heated for several hours at 80° C under nitrogen giving the $C_{20}$ enyne.

In a particular example, the following components were employed:

| | |
|---|---|
| $C_{15}$-acetylene (67.2% purity) | 9.9 grams (0.0317 mole) |
| Methyl-MgCl (1.25 M) | 27 ml (0.0338 mole) |
| CuCl | 3.52 grams (0.0356 mole) |

| -continued | |
|---|---|
| THF (dry) | 11 + 25 = 36 ml |
| Isoprene Chloroacetate | 6.4 grams (0.0396 mole) |
| DMF | 35 ml |

The Grignard reagent was added dropwise to a solution of 11 ml of THF (tetrahydrofuran) and the acetylene at less than 30°, followed by warming to 60° and maintaining this temperature for two hours. This was followed by cooling, addition CuCl, and addition of the chloroacetate with the remaining THF. The DMF is then added and the THF removed under vacuum heating up to 50°. The coupling reaction was carried out at about 90° for six hours, producing 3.0 grams of pure product (28% of theoretical yield).

Method B: An alternative method comprises forming a complex molecule of cuprous chloride and Honig's base

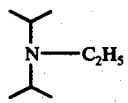

in DMF, the latter also having the $C_{15}$ acetylene compound dissolved therein. This forms the copper salt which is then reacted with "isoprene chloroacetate" (4a) as in Method A. Other aprotic solvents and combinations thereof can be employed. Also, other amines such as t-butyl amine can be employed. Yields of the $C_{20}$ enyne employing Method B are comparable to those employing Method A.

In this example, the following components were employed:

| $C_{15}$-acetylene | 20.6 grams |
|---|---|
| CuCl | 9.9 grams (0.10 mole) |
| Honig's Base | 14.2 grams (0.11 mole) |
| Isoprene Chloroacetate | 18.6 grams (0.115 mole) |
| DMF (dry) | 30 + 30 + 30 = 90 ml |

The base, CuCl and 30 ml DMF under nitrogen were mixed with the acetylene in an additional 30 ml of DMF, at about 45°. This mixture was heated to 50° and the chloroacetate in the remaining DMF was added. The reaction took place at 80°-85° for six hours. The yield was 14.1 grams of pure product or about 45% of theoretical.

Hydrogenation

The compound of formula (5) is next subjected to selective hydrogenation to convert the acetylenic bond to an ethylenic bond. This can be readily accomplished by a number of different catalysts, such as a nickel catalyst prepared from a nickel salt and $NaBH_4$, catalyst, or 5% palladium on barium sulfate in the presence of quinoline. Selective semihydrogenation is commonplace, for instance as to conditions, amounts and procedures. In this particular example, the reaction was run at one atmosphere. Analyses by nuclear magnetic resonance and vapor phase chromatography showed the correct structure in good quantity.

The product obtained was 3, 7, 11, 15-tetramethylhexadeca-2,5-dien-1-acetate (6), a $C_{20}$ dienol acetate.

Saponification of the $C_{20}$ Dienol Acetate to Dehydrophytol

The acetate of formula (6) is dissolved in 1-2% methanolic NaOH and allowed to stand for 12 hours at room temperature under nitrogen. The reaction mixture is then quenched with water, and the precipitated oil is taken up in hexane. The hexane solution after drying with anhydrous sodium sulfate or magnesium sulfate is concentrated under vacuum, and the residual oil can either be distilled under high vacuum or used as such in the subsequent steps. High yields of dehydrophytol [3, 7, 11, 15-tetramethylhexadeca-2,5-dien-1-ol (7)] were obtained. UV absorption showed no detectable conjugation. The product was chromatographed on alumina, which gave a pure material.

Condensation of Dehydrophytol with TMHQ to Yield Dehydro-Vitamin E

For the synthesis of dehydro-Vitamin E, 0.45 grams (1.54 millimoles) dehydrophytol of formula (7) is reacted with 0.23 grams (1.51 millimoles) trimethylhydroquinone to yield dehydro-Vitamin E following the procedure published in the *Journal of Organic Chemistry*, Volume 36, (19) pages 2910-12 (1971), by Wehrli, Fryer and Metlesics. Essentially the method involves first forming a TMHQ-$BF_3$ complex in methylene chloride (2 ml) containing one equivalent of nitromethane (0.090 ml) and no excess $BF_3$, by bubbling in the $BF_3$ and precipitating the complex. The dehydrophytol is then added with 3.5 ml of methylene chloride at $-20°$ C; and the reaction is carried out for a period at $-20°$ C, then at $-10°$ C, and finally at room temperature to yield dehydro-Vitamin E.

The dehydro-Vitamin E obtained is hydrogenated with platinum catalyst in methanol. Good yields of Vitamin E (8) (alpha-tocopherol) are obtained.

General Application of the Invention

The invention has been described with reference to the synthesis of dehydrophytol (7) employing hexahydropseudo-ionone as a starting material. Concepts of the invention are also applicable to the synthesis of perfume products and other intermediates such as dimethyloctanol and others. These products can be synthesized by coupling a reactant having the general formula:

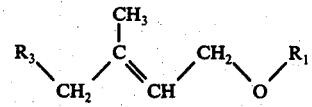

where $R_3$ is a halogen and $R_1$ is hydrogen or $COR_2$, $R_2$ being a lower alkyl, phenyl, substituted phenyl, or aralkyl with a second reactant derived from a statting compound of the general formula:

where $R_4$, $R_5$ and $R_6$ are hydrogen, alkyl, phenyl, substituted phenyl or aralkyl.

Preferably $R_1$ is $COR_2$, $R_2$ is methyl, $R_4$ is methyl and $R_6$ is hydrogen with $R_5$ being any of the following:

Table 1

1) methyl
2) 4-methylpentyl
3) 4,8-dimethyl-1,7-nonadienyl
4) 4,8-dimethyl-3,7-nonadienyl
5) 4,8-dimethyl-1,3-nonadienyl
6) 4,8-dimethyl-1-nonenyl
7) 4,8-dimethyl-3-nonenyl
8) 4,8-dimethyl-7-nonenyl
9) 4,8-dimethylnonyl
10) 4,8-dimethyl-1,3,7-nonatrienyl The products of the reaction will have the following general formula, $R_5$ being as previously defined:

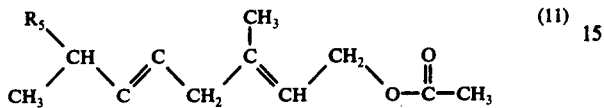

(11)

Selective partial or total hydrogenation and saponification of the reaction product then yields products with the following skeletons depending upon the structure of $R_5$.

Table 2

| $R_5$ Radical (from Table 1) | Skeleton of the Product |
|---|---|
| Group 1 | 3,7-dimethyloctanol |
| Group 2 | hexahydrofarnesol* |
| Groups 3 – 10 | dehydrophytol |

*3,7,11-trimethyldodecan-1-ol

By the term "skeleton", it is meant that the reaction product may be 3,7-dimethyloctanol (or any of the others listed in the right-hand column of Table 2) if the hydrogenation is complete; or alternatively, the reaction product may have some unsaturated sides remaining while maintaining, the same structure or arrangement of carbon atoms if the hydrogenation is less complete.

Compounds of formula (10) can be made by the known reaction of ketones with the alkali metal salts of acetylenes, and specifically by the steps outlined above with reference to hexahydropseudo-ionone. For instance, to produce the compound of formula (10) with the $R_5$ radicals listed in Table 1, the following ketones could be used:

Table 3

| $R_5$ Radical | Ketone |
|---|---|
| methyl | acetone |
| 4-methylpentyl | 6-methylheptan-2-one |
| 4,8-dimethyl-3,7-nonadienyl | geranyl acetone |
| 4,8-dimethyl-1,3,7-nonatrienyl | pseudo-ionone |

Thus, in a specific example, acetone is reacted with a compound such as lithium acetylide to produce a $C_5$-acetylenic carbinol

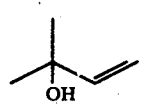

which, when reductively dehydroxylated by the reaction sequence used for going from the $C_{15}$-acetylenic carbinol to the $C_{15}$-acetylene, and coupled with isoprene chloroacetate, forms a basic $C_{10}$ skeleton capable of being hydrogenated and saponified to dimethyloctanol ($C_{10}H_{22}O$). Similarly, 6-methylheptan-2-one is reacted with lithium acetylide to produce a $C_{10}$ acetylenic carbinol having the formula:

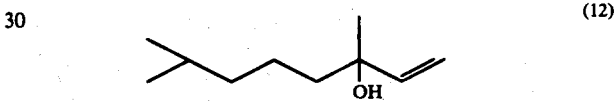

(12)

This compound when reductively dehydroxylated by the sequence described above and coupled with "isoprene chloroacetate" forms a basic $C_{15}$ skeleton capable of being hydrogenated and saponified to 3, 7, 11-trimethyldodecan-1-ol.

Having thus described the invention, what is claimed is:

1. The compound 3, 7, 11-trimethyldodeca-1,2-diene.

* * * * *

UNITED STATES PATENT AND TRADEMARK OFFICE
CERTIFICATE OF CORRECTION

PATENT NO. : 4,075,257

DATED : February 21, 1978

INVENTOR(S) : Ralph E. Close; William Oroshnik

It is certified that error appears in the above-identified patent and that said Letters Patent are hereby corrected as shown below:

Col. 2, line 62, change "number" to --numbering--. Col. 3, line 66, change the portion of the formulation reading "-4chloro-" to -- -4-chloro- --. Col. 5, line 58, after "$NaBH_4$," insert --Lindlar--. Col. 6, line 36, before "platinum" insert --a--; line 57, change "statting" to --starting--.

Signed and Sealed this

Sixth Day of June 1978

[SEAL]

Attest:

RUTH C. MASON
Attesting Officer

DONALD W. BANNER
Commissioner of Patents and Trademarks